(12) United States Patent
Zaromb et al.

(10) Patent No.: US 7,472,612 B2
(45) Date of Patent: Jan. 6, 2009

(54) AEROSOL COLLECTION APPARATUS AND METHOD

(76) Inventors: Solomon Zaromb, 9S 706 William Dr., Burr Ridge, IL (US) 60527; Dennis J. Martell, 7 Cider Hall La., Douglas, MI (US) 49406

( * ) Notice: Subject to any disclaimer, the term of this patent is extended or adjusted under 35 U.S.C. 154(b) by 118 days.

(21) Appl. No.: 11/473,748

(22) Filed: Jun. 23, 2006

(65) Prior Publication Data

US 2007/0113685 A1 May 24, 2007

Related U.S. Application Data

(63) Continuation-in-part of application No. 10/710,838, filed on Aug. 5, 2004.

(60) Provisional application No. 60/693,418, filed on Jun. 24, 2005, provisional application No. 60/481,184, filed on Aug. 6, 2003.

(51) Int. Cl.
*G01N 1/18* (2006.01)
*G01N 1/22* (2006.01)

(52) U.S. Cl. .................. 73/863.21; 73/31.01; 73/31.02; 73/31.03; 73/863.41

(58) Field of Classification Search ..... 73/31.01–31.07, 73/863, 863.21, 863.22, 863.41, 864.71
See application file for complete search history.

(56) References Cited

U.S. PATENT DOCUMENTS

| 3,061,100 | A  | * | 10/1962 | Fehlmann | ............ | 210/108 |
| 3,343,178 | A  | * | 9/1967 | Palmer | ............ | 210/360.2 |
| 3,344,623 | A  | * | 10/1967 | Eaman et al. | ............ | 68/12.19 |
| 5,534,161 | A  | * | 7/1996 | Tarr et al. | ............ | 210/744 |
| 6,230,572 | B1 | * | 5/2001 | Pui et al. | ............ | 73/863.21 |
| 6,347,527 | B1 | * | 2/2002 | Bailey et al. | ............ | 62/238.7 |
| 6,964,189 | B2 | * | 11/2005 | Carlson et al. | ............ | 73/28.02 |
| 7,174,767 | B2 | * | 2/2007 | Booker | ............ | 73/24.01 |
| 2002/0017107 | A1 | * | 2/2002 | Bailey et al. | ............ | 62/238.7 |
| 2006/0207573 | A1 | * | 9/2006 | Douyama et al. | ............ | 123/509 |
| 2007/0113685 | A1 | * | 5/2007 | Zaromb et al. | ............ | 73/863.21 |

* cited by examiner

*Primary Examiner*—David A. Rogers
(74) *Attorney, Agent, or Firm*—Solomon Zaromb

(57) ABSTRACT

Apparatus and methods for detecting the presence of an airborne chemical or biological analyte utilize:
 a substantially gas- and liquid-impermeable container;
 means for introducing a substantially analyte-free collection liquid into said container;
 means for rapidly sampling ambient air and transferring said analyte therefrom into said collection liquid, said sampling means comprising an air intake means and and an air venting means; and
 means for removing from said container an analyte-enriched collection liquid;
wherein said volume of air passes through a substantially horizontal air inlet and downward through a substantially vertical collector electrode tube with means for applying an electric field between said tube and a co-axial spiked wire- or rod-shaped discharge electrode.

Efficient wet electrostatic precipitation with efficient collection of captured particles into a tiny liquid volume are achieved by the use of a liquid flow system comprising a programmable reversible pump with a reversible filter and appropriate liquid connections and valves. Injection of water sprays into the air stream and onto the interior walls of the collector electrode permits thorough wetting of interior surfaces and efficient removal of residual captured particles.

20 Claims, 11 Drawing Sheets

Assembly 19 of Fig. 5, Including Intake Chamber 4 with High-Voltage Wire 2 and Air Intake 35, and Lower Liquid-Collection and Air Outlet Chamber 6 with Liquid Transfer Tubule 21.

WEP Components:

Discharge Electrode [1] with High-Voltage Wire [2];

Collector Tube [3] Connected to the Upper Air Intake Chamber [4] and Cyclonic Large Particles Trap [5];

Lower Liquid Collection Chamber [6] With Air Outlet [7]; and Air Exhaust Blower [8].

Collector Tube 3 with Upper Air Intake Chamber 4 and Liquid Pump Connection 20

Assembly 19 of Fig. 5, Including Intake Chamber 4 with High-Voltage Wire 2 and Air Intake 35, and Lower Liquid-Collection and Air Outlet Chamber 6 with Liquid Transfer Tubule 21.

Fraction of 1-Micron Fluorescent Beads Recovered from a Reversible Cellulose Acetate Filter with Different Back Flushing Volumes Enhancement of the Concentration of 1-Micron Fluorescent Beads Recovered from a Reversible Cellulose Acetate Filter with Different Back Flushing Volumes Fig. 11. Removal Efficiencies of the Cyclonic Trap

AEROSOL COLLECTION APPARATUS AND METHOD

REFERENCE TO RELATED APPLICATIONS

This is a continuation-in-part of provisional application Ser. No. 60/693,418, filed Jun. 24, 2005, which is a continuation-in-part of application Ser. No. 10/710,838, filed Aug. 5, 2004, which is a continuation-in-part of provisional application No. 60/481,184, filed Aug. 6, 2003, which is related to U.S. Pat. Nos. 5,328,851, 6,087,183, and 6,565,811 and to U.S. applications Ser. No. 08/377,966 [filed Jan. 25, 1995] and Ser. No. 09/611,744 [filed Jul. 7, 2000] now U.S. Pat. Nos. 6,762,060B1 and 6,642,057B1. The disclosures of all of said applications and patents are incorporated herein by reference.

BACKGROUND OF THE INVENTION

This invention relates to improved apparatus and methods for detecting harmful substances, whether airborne or grounded, whether biological or chemical, which may pose an immediate or long term hazard to human life or health.

The afore-cited patents and co-pending applications, disclose apparatus and methods for collecting various contaminants (including vapors and particles, chemical or biological) from a large volume of air into a small volume of carrier liquid, so as to permit or facilitate rapid and ultra-sensitive detection of traces of hazardous or illicit substances which may be otherwise difficult to detect. The collected contaminants may be either dissolved by or suspended in the carrier liquid.

The earliest apparatus of this type was intended mainly for the absorption of vapors by the carrier liquid and was therefore referred to as liquid-absorption air sampler. With subsequent use of the same apparatus for the collection of respirable particles, the term (absorption) became inappropriate, as the collected particles may remain suspended in the carrier liquid without being dissolved therein. Such apparatus and methods will therefore be referred to herein as (HTLAAS) for High-Throughput Liquid-Assisted Air Sampling, which applies to collected air contaminants which are either dissolved or suspended in a carrier liquid.

A good measure of the performance of HTLAAS devices is the concentration factor F, which is proportional to the ratio of the concentrations in the liquid carrier and in air of the monitored contaminant, hereinafter referred to as (analyte.) The concentration factor F is defined by the equation $$F = \epsilon S / v_L \quad [1],$$

where $\epsilon$ is the sampler's collection efficiency, S is its air sampling rate, and $v_L$ is the volume of liquid in which the analyte is collected. The concentration factor F can thus be enhanced by increasing $\epsilon$ and/or S or by decreasing $v_L$.

The need for efficient aerosol collectors has been appreciated for more than a decade both for all point bio-detection systems and for future chemical point detectors, where the term "point" applies to spots where samples are taken as opposed to remote detection. Several collectors have been developed and used by the military and first responders. However, recent incidents of bio-terrorism have revealed serious shortcomings of these collectors. When these were used in conjunction with immunoassay-based test strips, the resulting effective detection limit for anthrax bacilli was far above the known dangerous or lethal concentrations, so that inhalation of low but lethal doses of anthrax or other biological warfare [BW] aerosol agents could have been easily overlooked. Although several existing wetted wall cyclone aerosol collectors can remove a substantial fraction of particulates from a large volume of air (several cubic meters) and transfer them into a small liquid volume (a few milliliters) for analysis, their power requirements are high (400-500 watts)—driven by the need to collect particles as small as 1 micron. Cyclones and most inertial separation devices are intrinsically very inefficient at capturing small particles.

Somewhat of an exception may be the PHTLAAS [Portable HTLAAS] of U.S. Pat. No. 6,087,183, a variant of which was found to yield a collection efficiency of 66±3% for 1-micron particles and 84±4% for 4-micron particles at an air flow rate of 317 liters/minute, as reported by Kesavan, J.; Carlile, D.; Doherty, R. W.; Sutton, T.; and Hottell, A., "CHARACTERISTICS AND SAMPLING EFFICIENCY OF PHTLAAS™ AIR SAMPLER," ECBC-TR-267, US ARMY, 2002. When a similar sampler, hereafter referred to as "recent PHTLAAS", was operated at full power with a 12-volt battery, the measured power consumption was only 42 watts [3.5 amps at 12 volts]. The comparatively low power consumption of only 42 watts by the recent PHTLAAS is attributed to its unique flow pattern in which the direction of the air stream is partly reversed as it enters through the air intake, as disclosed in U.S. Pat. No. 6,087,183.

Although this recent PHTLAAS seems to compare favorably with other inertial-separation-type collectors, it still cannot match the much higher efficiencies that are obtainable with electrostatic precipitation [EP] technology for removing small particles from a gas [see, e.g., Altman, R.; Buckley, W.; and Ray, I.; "WET ELECTROSTATIC PRECIPITATION DEMONSTRATING PROMISE FOR FINE PARTICULATE CONTROL," Power Engineering, January-February, 2001, or Parker, K. R., editor; "Applied Electrostatic Precipitation," Chapman & Hall, London, 1997].

According to the latter references, wet EP [WEP] can achieve collection efficiencies of 99.9% for particles as small as 0.01 micron in size and for various gaseous species, including dioxins/furans, which could also assure capture of toxins and dry virus particles. The latter remain suspended in air long after evaporation of water from the droplets in which they were originally dispersed and may thus present a persistent not readily noticeable hazard. Therefore, an ability to collect dry virus particles should greatly enhance the effectiveness of biological agent detection systems.

Inertial separation devices, including the PHTLAAS, operate on altogether different principles than EP and consequently have different physical structures. Whereas the airflow within the PHTLAAS is highly turbulent and swirling rapidly, so as to impel particles towards the container wall by centripetal action, the flow in EP devices is substantially laminar, so as to permit high flow rates at rather low pressure drops and low power consumption.

The major reduction in power consumption that is expected from the use of EP yields not only major savings in the size, operating costs, and equipment cost of the resulting collectors, but also smaller and lighter instruments by reducing the size and weight of required batteries or else permits uninterrupted operation between battery replacements for longer time periods, thereby further increasing the utility of portable collectors.

SUMMARY OF THE INVENTION

In spite of their altogether different and maybe even incompatible basic operating principles and consequent differences between inertial and EP-based devices, it is an object of the present invention to provide PHTLAAS-EP apparatus and methods yielding improvements that would not be expected from either of these technologies alone.

It is an object of this invention to incorporate EP within the present PHTLAAS configuration with relatively minor modifications.

It is another object to effectuate modifications that permit an EP-activated PHTLAAS to operate as a continuous wet precipitator so as to result in a transfer of precipitated particles into a small volume of collection fluid.

It is an overall objective of the present invention to provide new aerosol collector devices which maximize the quantity of aerosol collected in the size range of 1-10 microns while reducing the portion of aerosol particles larger than 10 microns, and also keeping the overall equipment size, weight, cost and power requirements relatively small.

It is an object of the invention to provide an EP-based aerosol collection system sampling air at a high rate, e.g., >500 l/min, and capturing particles throughout the size range of 1-10 microns at a collection efficiency of >80%.

It is a further object of the invention to increase the collection efficiency and air sampling rate while reducing the power requirements and volume of the collection medium [water or an aqueous solution].

It is still another object of the invention to provide an inertial large-particle trap at the air intake[s] to prevent particles larger than 10 microns in size from entering the collector, so as to reduce interference from the larger non-respirable particles.

Other objects of our invention are to provide an electronically programmable interface between a collector and a detector, so as to yield an automated or quasi-automated collection-detection system, to reduce the size and weight of the overall system, and to further enhance the system's sensitivity by further increasing its collection efficiency and air sampling rate.

More objects of the invention will become apparent to professionals in the chemical and biological defense, law enforcement, health monitoring, disease control, industrial safety and hygiene, environmental, chemical, metallurgical, and related areas following perusal of the complete specification.

Briefly, the invention aims at effectuating modifications in the basic configuration of the PHTLAAS of U.S. Pat. No. 6,565,811 so as to convert it into an EP-based air sampler. These modifications consist of replacing the glass sampling tube of the PHTLAAS by an electrically conductive collector electrode tube, inserting a wire- or rod-shaped high-voltage discharge electrode co-axially with the collector electrode, and providing an air intake that is designed and disposed so as to yield a high air flow through the sampler at a low pressure drop and low power consumption. The low-pressure-drop high-air-flow intake is preferably situated near the top of the WEP, so as to yield a downward air flow. To rinse the interior of the collector tube, a small pressurized water spraying and swirling system washes down particles that deposited on these walls during a collection step. The same washing system can serve to decontaminate the sampler by injecting a spray of bleach solution instead of water and to subsequently remove the bleach from the system by injecting sprays of a neutralizing solution and of a rinsing liquid.

Upon turning on the power, sampled air is now drawn in through the modified intake and caused to flow downward through the collector tube. Also drawn in are sprayed water droplets yielding a liquid film on the inner surface of that electrode for either maintaining full electrode wetting during sampling or to help remove captured particles from the interior walls of the collector after the sampling.

Another important feature of our invention is minimization of the volume of collection liquid and concentration of the collected particles by recirculating the rinsings through an appropriate reversible filter which permits reuse of filtered liquid for rinsing purposes and collection of the particles retained by the filter within a tiny back flushing volume.

BRIEF DESCRIPTION OF THE DRAWINGS

The invention is best explained with reference to the drawings, in which.

DESCRIPTION OF THE PREFERRED EMBODIMENTS

Since inertial separation and EP operate on different physical principles, the two approaches would not be expected to share many common features. Nevertheless, the collector electrode in a cylindrical EP system bears a physical resemblance to the glass sampling tube of the PHTLAAS, and the latter's liquid wash-down and collection scheme is at least partly applicable to EP.

Figure 4:
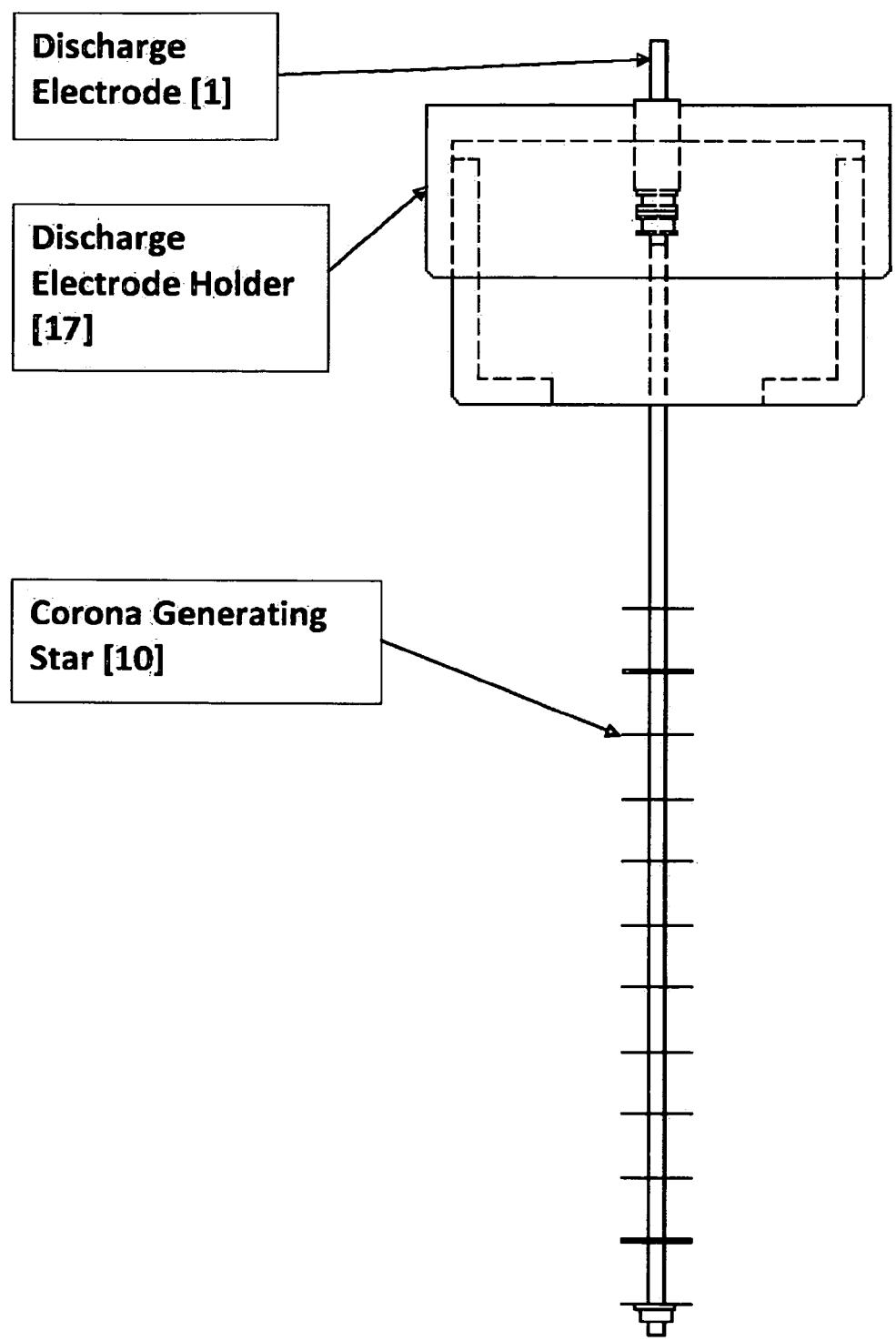
FIG. 4 shows a discharge electrode holder 17 with a high-voltage discharge electrode 1 that is to be inserted co-axially with the collector tube 3 of FIG. 1.

The collector electrode bears a similarity to the sampling tube of the PHTLAAS but with its inner surface electrically conducting. The main altogether new components are the central wire-or rod-shaped discharge electrode 1 of FIGS. 1 and 4, kept at a high negative or positive potential [possibly as high as 10 KV or higher], and a horizontal tubular air intake 35 of FIGS. 5 and 6, through which air can enter unimpeded at a high flow rate with a minimal pressure drop.

As in the PHTLAAS, a mist that is injected into air passing through the cylindrical tube 3 deposits on and fully wets the inner surfaces of the collector and forms a down-flowing film serving to rinse down deposited particles or unwanted bleach residue. However, collection of small aerosol particles is effected by a corona discharge from the central electrode 1 generating ionized particles which are driven by an electric field towards the interior wall of the electrically grounded collector electrode 3 [FIGS. 1, 5 and 6].

For this scheme to work optimally, the following factors need to be ascertained:

Proper Operation of the EP Electrodes. To assure collection of at least 80% of particles 1-10 microns in size at an airflow rate of at least 500 l/min, the electrodes and applied voltage must be designed and adjusted so as to generate a sufficient corona to ionize most of the particles in the air stream and a sufficient electric field to deposit most of these particles at the collector electrode. The latter's length and diameter must be such as to allow an adequate residence time for most particles to reach it rather than be carried away with the air stream.

The performance with negative and positive discharge electrode voltages can be compared with a view to minimizing undesirable ozone formation and spark discharges.

The preceding discussion outlines the basic features of the PHTLAAS-EP system of this invention.

Figure 5:
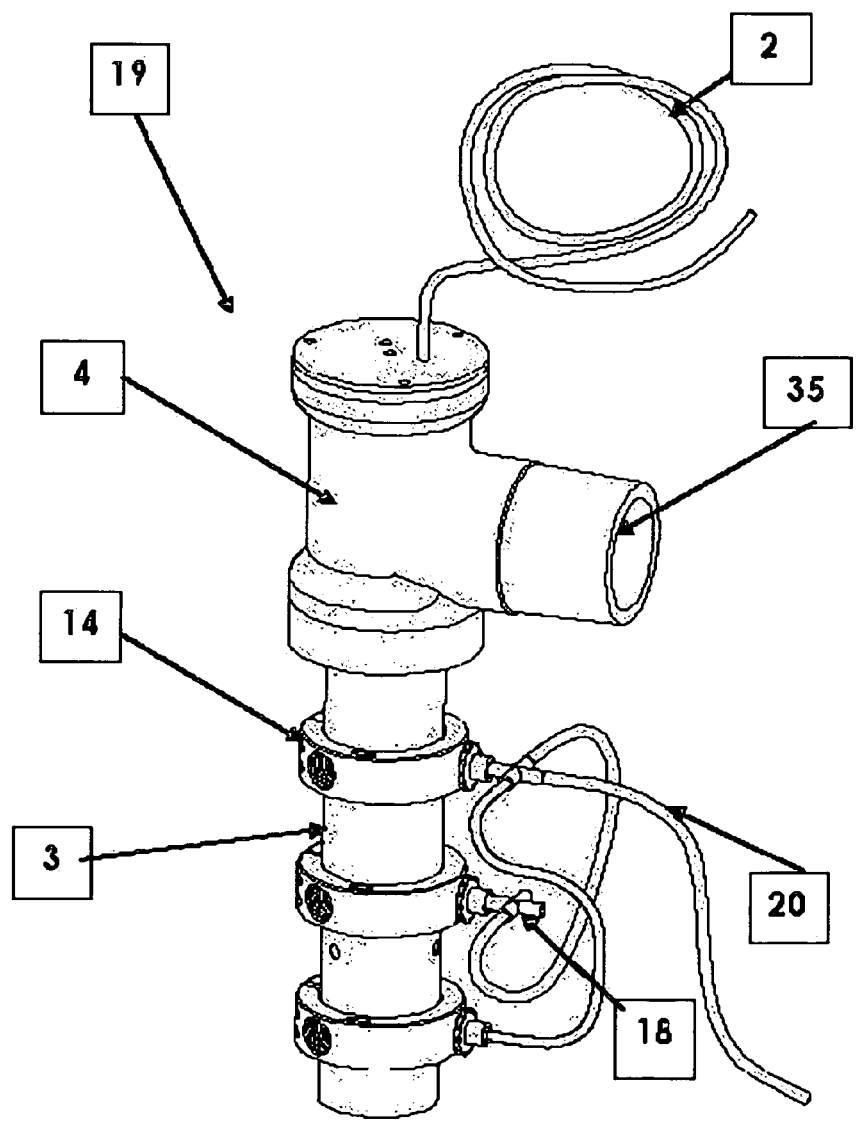
FIG. 5 shows the collector tube 3 of FIG. 1 with an upper air intake chamber 4 and connections 20 to a liquid pump.
Figure 6:
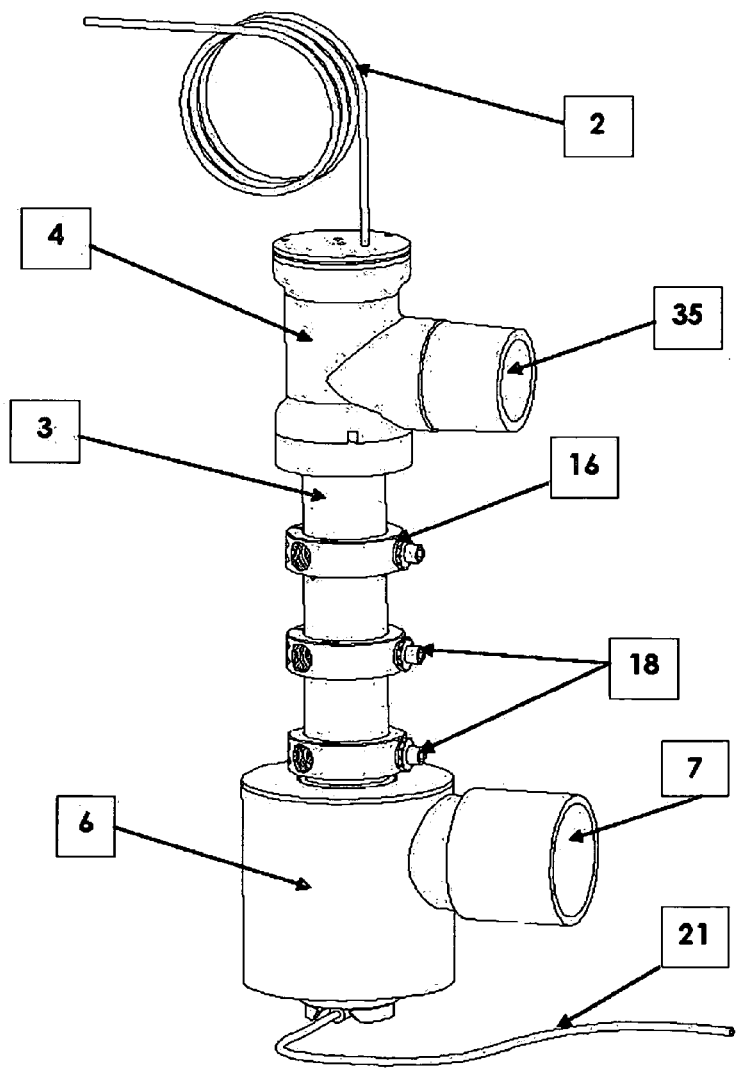
FIG. 6 shows the assembly 19 of FIG. 5 with a bottom-end liquid collection chamber 6 and air outlet 7.

As mentioned above, the inertial-type PHTLAAS comes close to meeting requirements for an aerosol collection system sampling air at a rate of at least 500 l/min and capturing particles throughout the size range of 1-10 microns at a collection efficiency of at least 80%. However, a major gain in energy efficiency is achieved with an EP-based system by replacing the slanted intake of the PHTLAAS by a horizontal radially directed low-pressure-drop air intake 35 [FIGS. 5 and 6] and adjusting the airflow rate therethrough to above 500 l/min with minimal blower power; replacing the glass sampling tube of the PHTLAAS by a grounded tubular collector electrode 3 [FIGS. 1, 5 and 6]; and inserting an axial discharge electrode 1 [FIGS. 1 and 4], with these electrodes connected to opposite terminals of a high-voltage power supply [not shown]. These modifications are detailed as follows:

Modification 1: FIG. 5 shows an assembly 19 comprising a collector tube 3 with an upper air intake chamber 4 and liquid pump connections 20. FIG. 6 shows assembly 19 with intake chamber 4, high-voltage wire 2, air intake 35, and a lower liquid-collection and air outlet chamber 6 with liquid transfer tubule 21. To provide an EP air intake, a sizable radial opening, e.g., 2" in diameter, is made in the upper chamber 4 [FIGS. 1, 5 and 6] and a straight tubular inlet 35 of the same diameter is fitted into it [FIGS. 5 and 6]. Intake 35 replaces and differs in two major ways from the slanted intake of the PHTLAAS. It is not only horizontal as in FIGS. 5 and 6, but it also directs the air into chamber 4 first radially towards the axis of the cylindrical configuration and then laminarly downward, so as to minimize resistance to airflow. Therefore, the power needed to draw air through intake 35 is far lower than what would be required to achieve a comparable flow rate through the PHTLAAS inlet. The power, i.e., voltage and current, fed to the air blower 8 of FIG. 1 can then be adjusted to yield higher flow rates through intake 35.

Modification 2: To properly wet and rinse the collector electrode 3 of FIGS. 1, 5 and 6, a novel approach is used to wet the walls with commercially available misters and to wash the walls down with a swirling action. Swirl needles 11 are placed at a 15 degree angle and spaced 120 degrees apart. In this way, the water hits the wall of the tube and swirls its way toward the bottom [FIG. 2]. The sprayers 13 are commercially available misters used for outdoor cooling. The water pressure is boosted to 30 psi and directed to the sprayers. There are nine sprayers evenly spaced along the collector tube 3 in three rows of three sprayers each 120 degrees apart. The sprayers 13 are held in place along tube 3 by three split rings 14 that are threaded to accommodate sleeves 16 that hold the sprayers and seal against the tube 3 [FIG. 3] and form tubing connections 18.

Modification 3: An accurately centered and well insulated discharge electrode 1 with corona generating stars 10 [FIGS. 1 and 4] in an electrode holder 17 [FIG. 4] is inserted through the top of the upper chamber 4 of FIGS. 1, 5 and 6. A length of high-voltage wire 2 attached to electrode 1 [FIGS. 1, 4 and 5] can be safely connected to the high-voltage terminal of an adjustable regulated High-Voltage DC power supply.

Figure 2A:
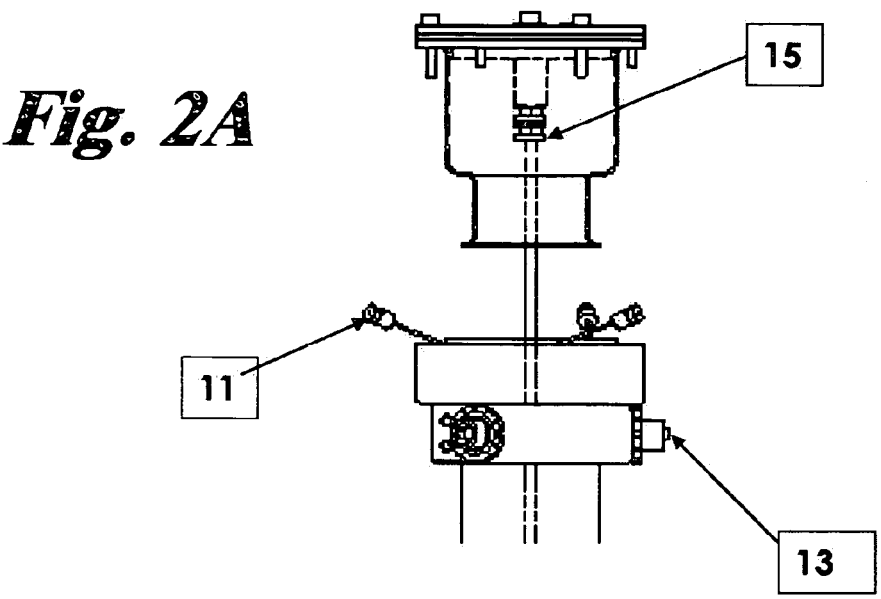
FIG. 2A shows details of the upper central portion of FIG. 1.
Figure 2B:
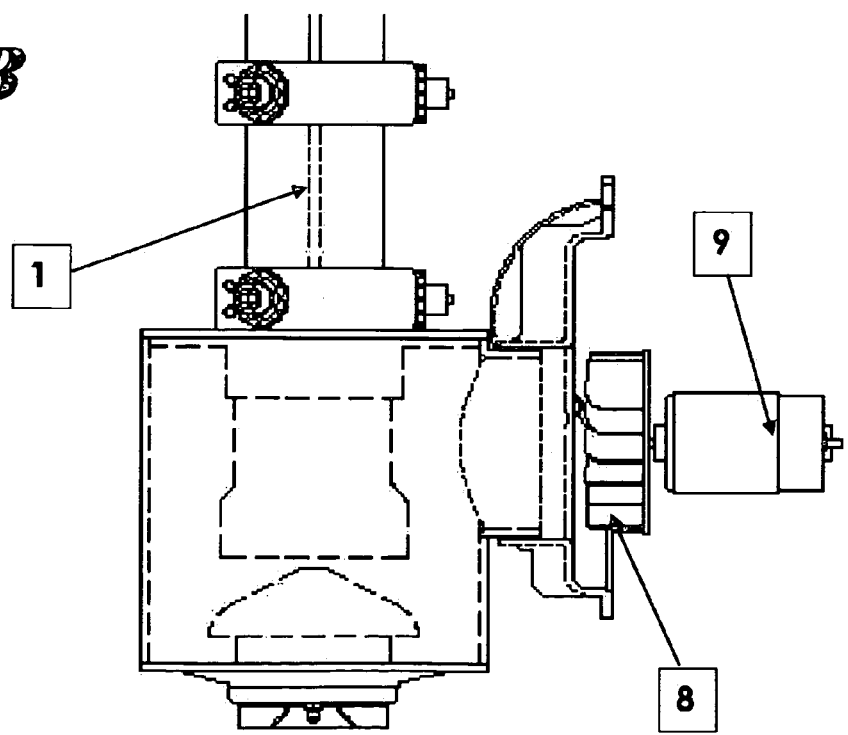
FIG. 2B shows details of the lower portion of FIG. 1.

To prevent shorting on the surface of a ceramic insulator that is separating the positive and negative electrodes it is important to keep the insulator clean and dry, preferably in a high-voltage shield 15 [FIG. 2] whose design is similar to that described in our co-pending application Ser. No. 10/710,838, filed Aug. 5, 2004.

The air sampling rate is varied by adjusting the voltage across the motor 9 of exhaust blower 8, as has been done with the inertial-type PHTLAAS. The voltage between electrodes 1 and 3 is varied by tuning the adjustable High-Voltage Power Supply.

EXAMPLE 1

For collection efficiency measurements, we use suspended 1-micron fluorescent beads obtained from Duke Scientific Corporation, Palo Alto, Calif. 94303. The fluorescent beads permit direct measurements with the aid of a fluorometer of the amounts of particles captured in the collection medium. The concentrations of particles in the sampled air are measured with the aid of a reference filter and their variations within our 3,000-liter test chamber are monitored with an Aerodynamic Particle Sizer [APS] instrument.

The described system was assembled, tested, and fine-tuned as follows:

1. The following test procedure was worked out:
   a. Circulate the contents of the test chamber through a HEPA filter for 10 minutes to reduce the particles count to a negligible value as measured with our APS [TSI Model 3310 Aerodynamic Particle Sizer] instrument.
   b. With the fans in the test chamber turned on, inject into the chamber about 1.2 ml of a standard suspension of 1.0-micron fluorescent latex particles through a nebulizer over a 5-minute period.
   c. Before starting the sampling operation, adjust the settings of pump 26 to assure a drainage rate from the walls of the collector electrode of at least 1 ml/minute.
   d. Run the sampler for 5 minutes at an airflow rate of 510 l/min. A reference filter placed near the inlet of the WEP is also set to draw air at the rate of 20 l/min during this 5-minute time period simultaneously with the WEP sampler. Also, during the same 5-minute period use the APS instrument to measure the concentrations of 1-micron particles at the entrance and exit from the WEP thereby determining the retention of these particles by the WEP.
   e. Flush down the walls of the collector tube by setting the pump to produce bursts of 3-10 ml of water at intervals of 5-20 seconds. Collect the first sample at the end of the 5-minute collection and subsequent rinse samples at half-minute intervals.
   f. Compare the fluorescence of the test and rinse samples with that of the suspension obtained from the reference filter.

The following table shows the retention of 1-micron particles by the WEP for two different airflow rates and for various high-voltage inputs using 1.5"ID and 2"ID 10"long collector tubes:

Measured Removal Efficiency of 1-Micron Particles for Various Sampling Rates and High Voltage Power Inputs

| Flow Rate [L/min] | High-Voltage Power [Watts] | Removal Efficiency [%] |
| --- | --- | --- |
| 255 | 6 | 89.5 [84-94] |
| 255 | 7 | 95.8 ± 0.1 |
| 255 | 9 | 96-98 |
| 510 | 9 | 80 |
| 510 | 15 | 90 |
| 510 | 17 | 91 |
| 510 | 20 | 94 |
| 510 | 22 | 95 |

According to these data, a high-voltage power input of 15 watts may suffice to retain in the tested WEP system about 90% of sampled 1-micron particles.

Our fluorescence measurements also indicate that >90% of the retained particles can be collected by the bursts of the above Step e.

Figure 3:
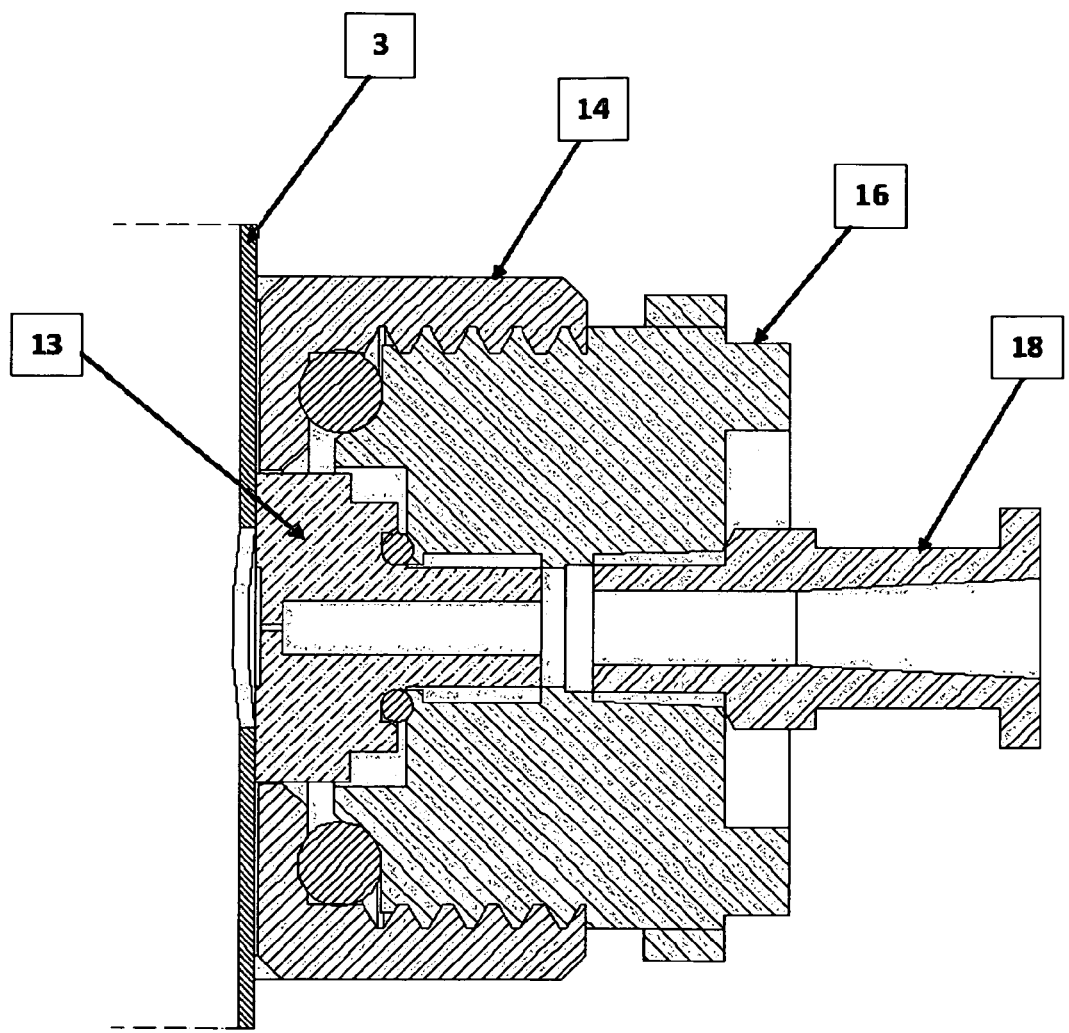
FIG. 3 shows one of the sprayers 13 of FIG. 2.
Figure 7:
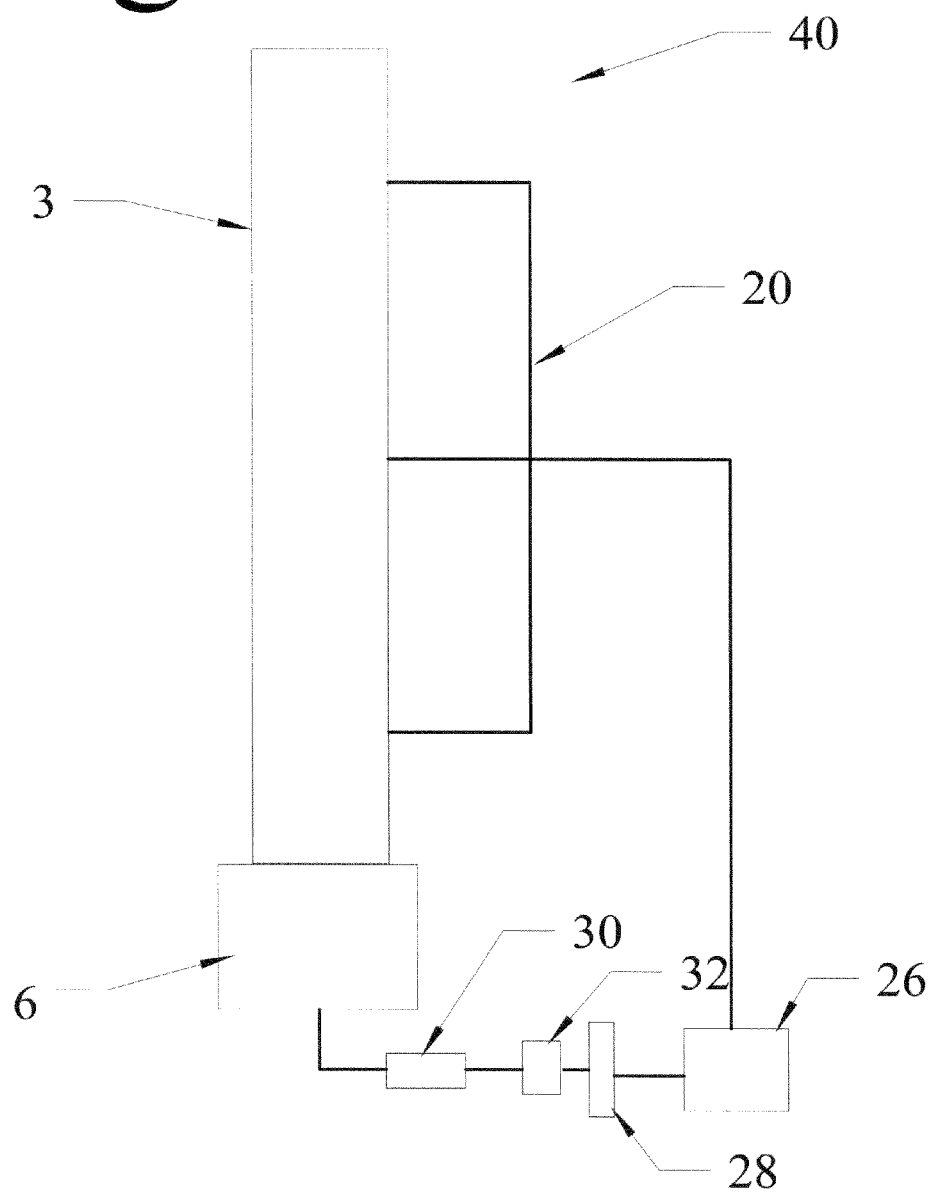
FIG. 7 is a block diagram of the liquid flow system for controlling the wetting and rinsing of the inner surface of the collector tube of FIG. 1 and for concentrating the particles captured by the WEP into a minimal volume of liquid.

However, to collect the captured particles within a small volume of water $v_L$, as is required to achieve a high concentration factor F according to Equation 1, we resort to the flow system 40 of FIG. 7, in which liquid draining from chamber 6 is drawn through a check valve 30, two-way valve 32 and reversible filter 28 into the reversible peristaltic pump 26 and hence through connections 20 back into the swirl needles 11 and sprayers 13 of FIGS. 2 and 3. To collect the captured particles into a small volume $v_L$, pump 26 is set to inject 1-5 ml of filtrate back through filter 28 so as to back flush all or most of the retained particles. Check valve 30 then prevents the concentrated suspension from flowing back into chamber 6, while two-way valve 32 is set to direct that suspension to a detector, syringe or storage vial. Also, during a decontamination step, a second two-way valve between filter 28 and pump 26 [not shown] may serve to prevent any bleach-containing solution from reaching the recirculating system by directing it into a waste container.

Figure 8:
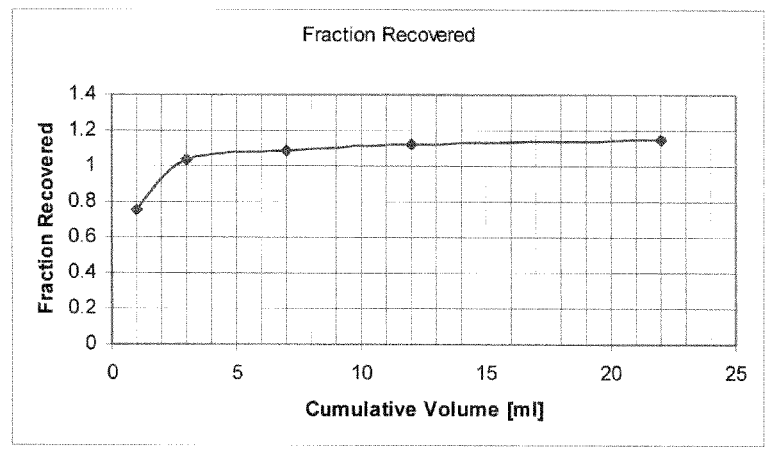
FIG. 8 shows the fraction of 1-micron fluorescent beads recovered from a reversible cellulose acetate filter with different back flushing volumes.
Figure 9:
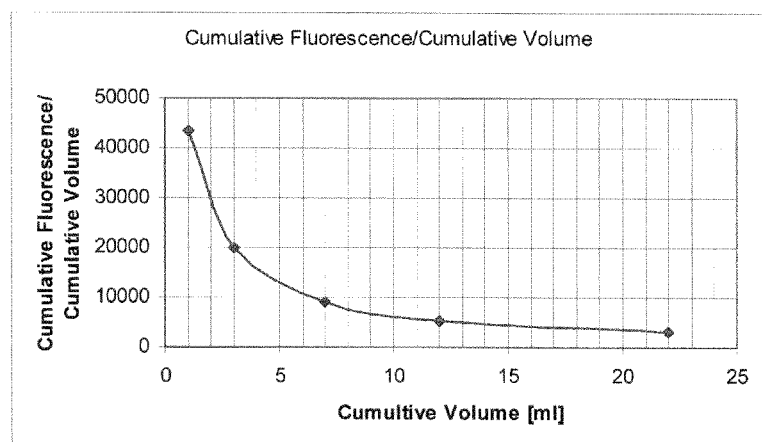
FIG. 9 shows the enhancement of the concentration of 1-micron fluorescent beads recovered from a reversible cellulose acetate filter with different back flushing volumes.

To test the afore-described back-flushing approach, 60 ml of a dilute suspension of 1-micron fluorescent particles were forced through a 25-mm diameter cellulose acetate filter with 0.8-micron pores [Advantec MFS, Part number C080A047A] and back flushed with measured volumes of filtrate. FIGS. 8 and 9 show that all or most of the filtered particles were recovered within a volume of about 3 ml, which constitutes a concentration enhancement by a factor of 60 ml/3 ml=20, and that about 75% were recovered within a volume of only 1 ml, yielding a concentration enhancement of 0.75×60 ml/1 ml=45. Our invention thus results in major enhancements in concentration factor by not only increasing the collection efficiency E but by major reduction in the volume $v_L$ of Eq 1.

Figure 1:
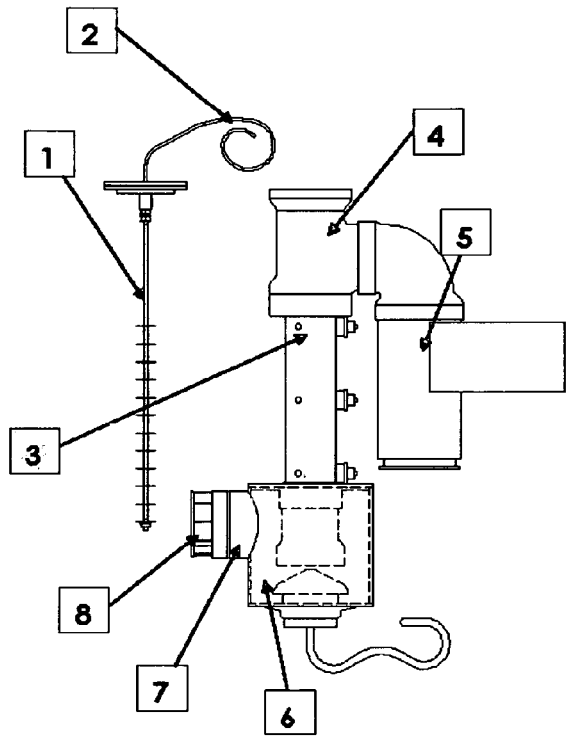
FIG. 1 shows most main components of a WEP system.
Figure 10:
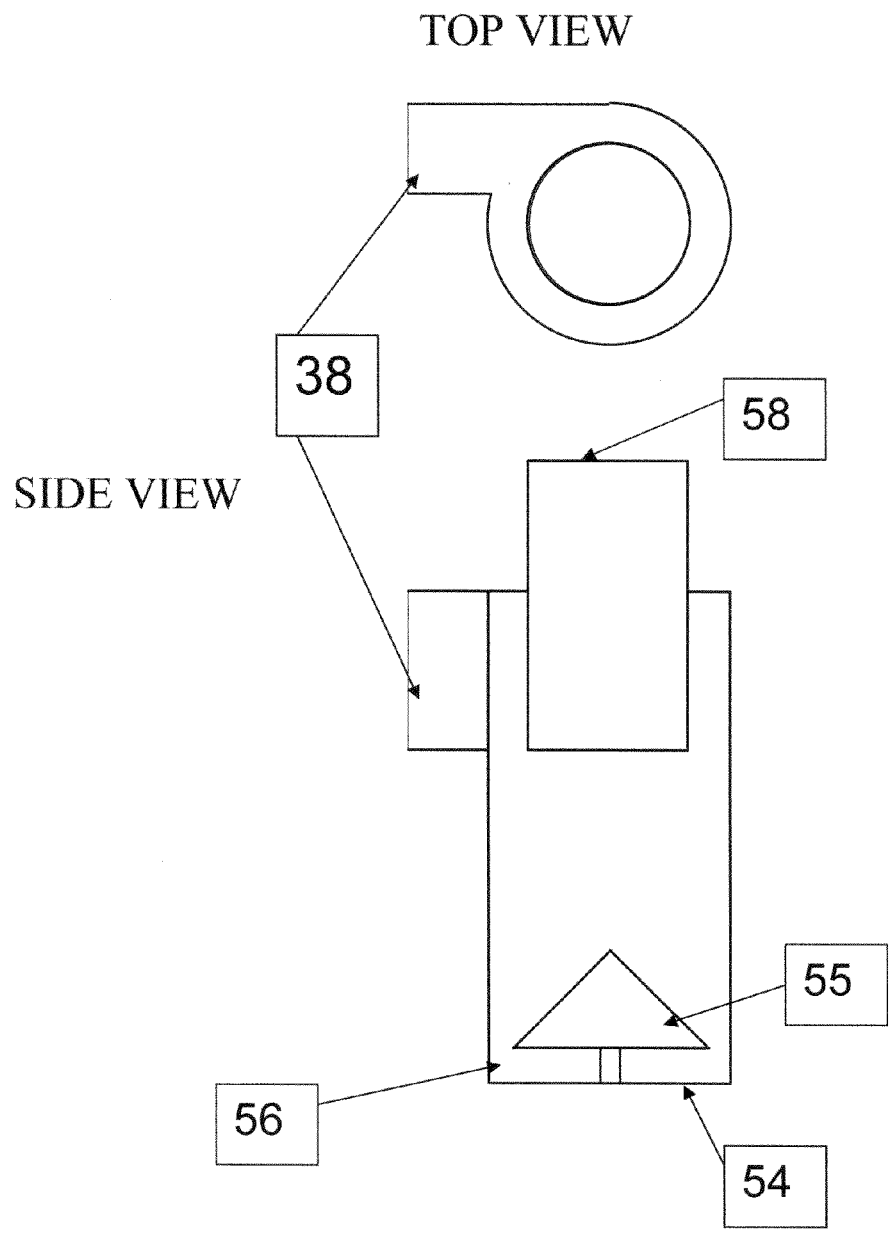
FIG. 10 shows a schematic design of a cyclonic large particles trap.
Figure 12:
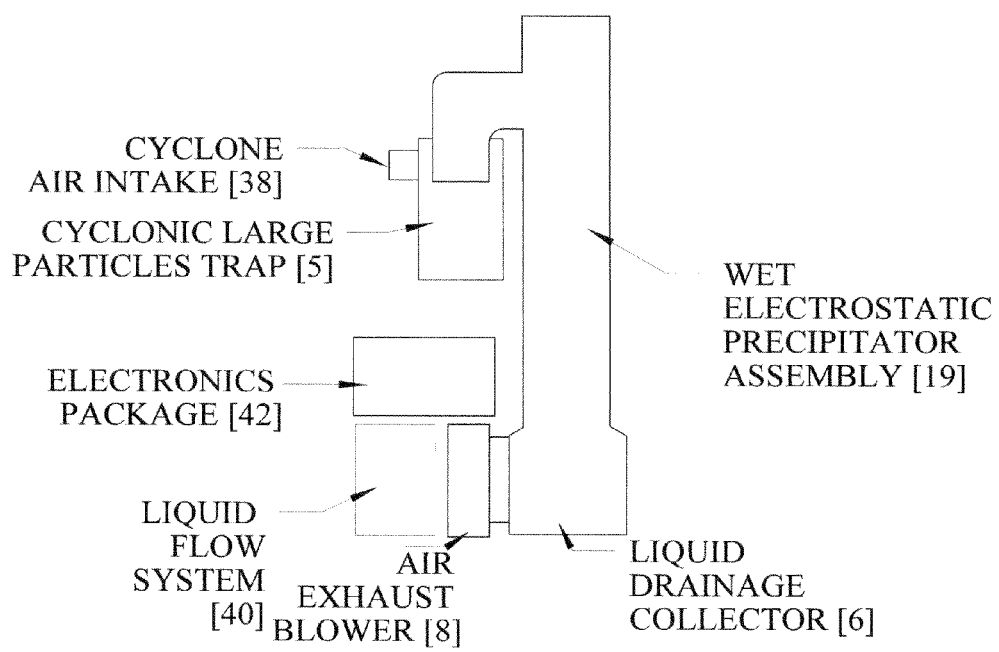
FIG. 12 is a block diagram of the layout of all the components of a briefcase-size fully self-contained and operational WEP system.

The APS instrument was also used to determine the removal efficiencies of particles in the size range of 1 to 17.5 microns using the cyclone 5 of FIGS. 1, 10, and 12. As shown in FIGS. 10 and 12, the sampled air enters cyclone 5 through inlet 38 and exits through outlet 58 either directly or through an elbow connection into inlet 35 of the upper chamber [FIG. 6]. The particles which are trapped by cyclone 5 accumulate in the space 56 beneath the conical baffle 55 and can be disposed of by pulling out the removable base 54.

Figure 11:
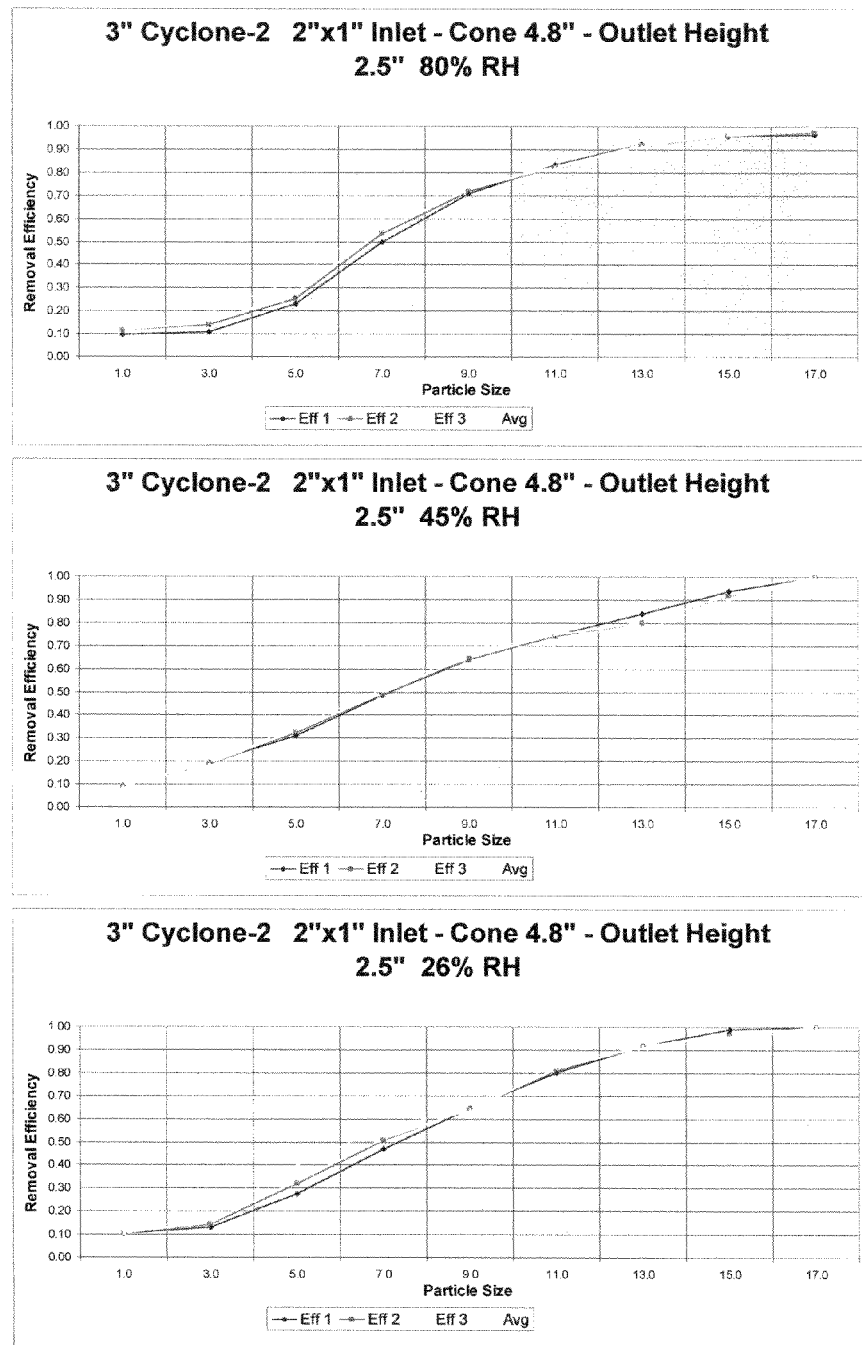
FIG. 11 shows the removal efficiencies of particles in the size range of 1-17.5 microns by the trap of FIG. 10.

The dependence of removal efficiency on particle size is shown in FIG. 11 for three different humidities. Cyclone 5 can thus be seen to remove 70-90% of particles in the range of 10-14 microns and >90% of those larger than 15 microns in size, but also 10-30% in the range of 1-5 microns and 30-70% of 6-9 microns in size. The substantial losses of particles in the 6-9 microns range are partly counterbalanced by the WEP's higher collection efficiency [close to 100%] for these particles.

All the above described components can be fitted into a briefcase-size package using the layout of FIG. 12, which includes an electronics package 42 comprising an already mentioned high-voltage power supply [not shown], a 24-volt battery pack [not shown], and control circuitry [not shown].

The afore-disclosed apparatus and methods can be used in various ways depending on the hazards which are to be monitored or detected.

The increased flow rate and collection efficiency with decreased power consumption and reduced liquid volume will yield enhanced detection sensitivity and lesser weight of the resulting EP-based devices. The reported ability of wet EP systems to collect particles as small as 0.01 micron, and many gaseous species, such as dioxins/furans, at efficiencies of >90% will extend the demand for such devices even further by making them also applicable to the capture and detection of toxins and dry virus particles.

The high airflow rates and collection efficiencies which are achievable with WEP technology not only for particles 1-10 microns in size but also for submicron particles render the PHTLAAS-EP applicable to ultra-sensitive detection of not only cellular pathogens, such as anthrax or tuberculosis bacilli, but also of the much smaller toxins and dry virus particles. The latter may pose a serious hazard following vaporization of the droplets in which they were originally dispersed. The capability to collect toxins and dry virus particles will therefore greatly strengthen the arsenal for defense against biological warfare agents.

The PHTLAAS-EP could be integrated into military field detectors, be helpful in other government activities, such as Treaty Verification, Domestic Preparedness, Demilitarization, and Homeland Defense, all of which will benefit from a smaller, lighter, more effective, and more energy-efficient collector which may capture not only single-cell pathogens but even dry virus particles and biological toxins. Civilian applications are also anticipated in many areas, such as medical monitoring, food packaging, and home inspection.

In the hands of first responders, the PHTLAAS-EP of this invention in conjunction with appropriate sensing means should provide the earliest possible post-exposure indication of a biological agent [BA] threat to facilitate diagnosis and treatment within the incubation period of most BAs, especially when used in conjunction with bio/non-bio or class-based detection that will indicate where to sample and when to analyze samples. Furthermore, civilian use of the technology for standard Industrial Hygiene practice should allow monitoring of HVAC systems for legionnaire's disease, molds, etc.

There will now be obvious many variations and modifications of the afore-disclosed embodiments to persons skilled in the art. It will be obvious that similar approaches can apply to the detection and monitoring of illicit drugs and many hazardous substances, e.g., comprising cadmium, zinc, chromium, uranium, or compounds of these metals, miscellaneous carcinogens, and other toxic contaminants, that can be either absorbed directly in a suitable liquid extractant or solubilized therein from collected airborne particulates.

The invention claimed is:

1. Apparatus for detecting the presence of an airborne chemical or biological analyte comprising:
   a substantially gas- and liquid-impermeable container;
   means for introducing a substantially analyte-free collection liquid into said container;
   means for rapidly sampling a volume of ambient air and transferring said analyte therefrom into said collection liquid, said sampling means comprising an air intake means and and an air venting means; and
   means for removing from said container an analyte-enriched collection liquid;
   wherein said volume of air passes in an air stream through a substantially horizontal air inlet and downward through the interior of a substantially vertical collector electrode tube with means for applying an electric field between said tube interior and a co-axial spiked wire- or rod-shaped discharge electrode.

2. The apparatus of claim 1, wherein said horizontal air inlet is such as to allow air to pass unimpeded at a high flow rate with a minimal pressure drop, said intake directing the air first radially towards the axis of a cylindrical collector tube and then laminarly downward, so as to minimize resistance to airflow.

3. The apparatus of claim 1, wherein said discharge electrode is kept at a high negative or positive potential, even as high as 10 KV or higher.

4. The apparatus of claim 3, wherein collection of small aerosolized particles is effected by a corona discharge from said co-axial electrode generating ionized particles which are driven by an electric field towards the interior wall of an electrically grounded collector electrode.

5. The apparatus of claim 4, wherein said collector and discharge electrodes and applied voltage are so designed and adjusted as to generate a sufficient corona to ionize most of the particles in said air stream and a sufficient electric field to deposit most of these particles at the collector electrode.

6. The apparatus of claim 5, wherein the length and diameter of said collector electrode are such as to allow an adequate residence time for most particles in said sampled air volume to reach its interior wall rather than be carried away with the air stream.

7. The apparatus of claim 1, including means for concentrating particles from said analyte-enriched collection liquid into a tiny liquid volume which comprises:
   a programmable reversible pump;
   a reversible filter;
   and appropriate liquid connections and valves,
   such as to allow removal of most of said analyte-enriched collection liquid followed by back-flushing of the retained particles through said reversible filter with said tiny liquid volume.

8. The apparatus of claim 7, comprising:
   a collection chamber for gathering said analyte-enriched collection liquid and feeding it to a reversible filter;
   a reversible pump for first filtering said analyte-enriched liquid and thereafter injecting a small volume of filtrate back through said reversible filter so as to back flush all or most of the retained particles;
   a check valve to prevent the resulting concentrated suspension from flowing back into said chamber; and
   a two-way valve set to direct that suspension to a detector, syringe or storage vial,
   whereby the volume of said analyte-enriched collection liquid is reduced and the concentration of collected particles is increased at least tenfold.

9. The apparatus of claim 7, comprising:
   a water spraying and swirling system for washing down particles deposited on collector tube walls and gathering the washings in a collection chamber;
   means for passing the washings through said reversible filter; and
   means for recirculating the filtered liquid and its reuse for rinsing purposes and collection of the particles retained by the filter within a tiny back flushing volume.

10. Apparatus of claim 1 comprising injection of water sprays into the air stream and/or onto the interior walls of the collector electrode to effectuate thorough wetting of interior surfaces and efficient removal of residual captured particles.

11. The apparatus of claim 10, comprising a pressurized water spraying and swirling system for washing down particles deposited on collector tube walls.

12. The apparatus of claim 11, wherein said washing system comprises means for decontaminating the sampler by injecting a spray of bleach solution instead of water and for subsequently removing the bleach from the system by injecting sprays of a neutralizing solution and of a rinsing liquid.

13. The apparatus of claim 11, wherein said washing system comprises swirl needles spaced at equal angles apart around the same circumference and placed at an approximately 15 degree angle downward from the horizontal plane, so as to cause exiting water to hit the wall of the tube and swirl its way toward the bottom.

14. The apparatus of claim 11, wherein said washing system comprises at least nine sprayers evenly spaced along the collector tube in at least three horizontal rows of at least three sprayers, each at equal angles apart, operating under a water pressure.

15. The apparatus of claim 14, wherein said sprayers are held in place by split rings that are threaded to accommodate sleeves that hold the sprayers and seal against corresponding openings in the collector tube.

16. A method for detecting the presence of an airborne chemical or biological analyte which comprises:
   introducing a substantially analyte-free collection liquid into a substantially gas-and liquid-impermeable container;
   rapidly sampling ambient air and transferring said analyte therefrom into said collection liquid, said container comprising an air intake means and and an air venting means; and
   removing from said container an analyte-enriched collection liquid;
   wherein said sampling step comprises passing air through a substantially horizontal air inlet and downward through the interior of a substantially vertical collector electrode tube while applying an electric field between said tube interior and a co-axial spiked wire-or rod-shaped discharge electrode.

17. The method of claim 16, comprising the steps of drawing in sprayed water droplets through the collector tube so as to yield a liquid film on the inner surface of that electrode for either maintaining full electrode wetting during sampling or to help remove captured particles from the interior walls of the collector after the sampling.

18. The method of claim 16, comprising the steps of wetting the interior walls of the collector electrode with misters and washing them down with a swirling action.

19. The method of claim 16, wherein said method is used to capture and detect particles as small as 0.01 microns.

20. The method of claim 19 wherein the particles are toxins, dry virus particles, or hazardous gaseous species.

* * * * *